(12) United States Patent
Dunfee et al.

(10) Patent No.: US 11,204,362 B2
(45) Date of Patent: Dec. 21, 2021

(54) SINGLE-PIECE TRANSFER ARM STRUCTURE FOR ANALYTICAL INSTRUMENTATION

(71) Applicant: Siemens Healthcare Diagnostics Inc., Tarrytown, NY (US)

(72) Inventors: William D. Dunfee, Newark, DE (US); Amanda H. Schaffers, Cary, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 480 days.

(21) Appl. No.: 16/075,539

(22) PCT Filed: Feb. 16, 2017

(86) PCT No.: PCT/US2017/018049
§ 371 (c)(1),
(2) Date: Aug. 3, 2018

(87) PCT Pub. No.: WO2017/142987
PCT Pub. Date: Aug. 24, 2017

(65) Prior Publication Data
US 2019/0041416 A1 Feb. 7, 2019

Related U.S. Application Data

(60) Provisional application No. 62/297,264, filed on Feb. 19, 2016.

(51) Int. Cl.
*G01N 35/10* (2006.01)
*G01N 1/14* (2006.01)
(Continued)

(52) U.S. Cl.
CPC .......... *G01N 35/1011* (2013.01); *A61B 17/00* (2013.01); *B01L 3/02* (2013.01);
(Continued)

(58) Field of Classification Search
None
See application file for complete search history.

(56) References Cited

U.S. PATENT DOCUMENTS

| 1,528,536 A | 3/1925 | De Walt |
| 2,673,273 A | 3/1954 | Vasold |

(Continued)

FOREIGN PATENT DOCUMENTS

| CN | 102661888 A | 9/2012 |
| CN | 202793855 A | 3/2013 |

(Continued)

OTHER PUBLICATIONS

PCT International Search Report and Written Opinion dated May 8, 2017 (8 Pages).

(Continued)

*Primary Examiner* — Benjamin R Whatley
*Assistant Examiner* — Curtis A Thompson

(57) ABSTRACT

Embodiments are directed to a single piece radial transfer arm for use in a clinical analyzer in an in vitro diagnostics (IVD) environment. The transfer arm is comprised of a chassis or elongated, rigid member that provides structural and aesthetic properties, acting as both a mounting base and a cover for transfer arm components. The elongated, rigid member is a single component, such as a single piece of injection-molded plastic. The elongated, rigid member has a top surface, a bottom surface, sidewalls, a pivot end, and a component end. One or more access holes and/or internal component mounting locations are provided for mounting one or more components on the bottom surface. A plurality of radial configuration mounting locations are provided on the bottom surface to allow for multiple radial distances between a pivoting axis of the transfer arm and an attached probe to accommodate arcs of different radii.

16 Claims, 8 Drawing Sheets

(51) Int. Cl.
    *G01B 21/16*    (2006.01)
    *G01N 33/48*    (2006.01)
    *B01L 3/02*     (2006.01)
    *B26D 1/00*     (2006.01)
    *A61B 17/00*    (2006.01)
    *B60S 1/40*     (2006.01)
    *G01N 1/10*     (2006.01)
    *G01N 35/04*    (2006.01)
    *G01N 1/38*     (2006.01)
    *G01F 23/18*    (2006.01)
    *G01N 1/00*     (2006.01)
    *G01N 1/28*     (2006.01)
    *G01N 35/02*    (2006.01)

(52) U.S. Cl.
    CPC . *B26D 1/00* (2013.01); *B60S 1/40* (2013.01);
    *G01B 21/16* (2013.01); *G01F 23/18* (2013.01);
    *G01N 1/00* (2013.01); *G01N 1/10* (2013.01);
    *G01N 1/14* (2013.01); *G01N 1/28* (2013.01);
    *G01N 1/38* (2013.01); *G01N 33/48* (2013.01);
    *G01N 35/02* (2013.01); *G01N 35/04*
    (2013.01); *G01N 35/10* (2013.01)

(56) References Cited

U.S. PATENT DOCUMENTS

| | | | | | |
|---|---|---|---|---|---|
| 3,529,158 | A | * | 9/1970 | Helmut | G01N 23/203 250/308 |
| 3,801,283 | A | * | 4/1974 | Shapiro | G01N 15/042 422/64 |
| 3,849,829 | A | | 11/1974 | Wubbe | |
| 3,858,450 | A | * | 1/1975 | Jones | G01N 35/1097 73/863.72 |
| 4,046,511 | A | * | 9/1977 | Stabile | G01N 35/1083 422/64 |
| 4,325,909 | A | | 4/1982 | Coulter et al. | |
| 4,344,768 | A | * | 8/1982 | Parker | G01N 35/1095 436/43 |
| 4,423,328 | A | * | 12/1983 | Spongr | G01N 23/203 250/358.1 |
| 5,304,201 | A | | 4/1994 | Rice | |
| 2003/0180185 | A1 | * | 9/2003 | Rose | G01N 30/12 422/70 |
| 2004/0007107 | A1 | | 1/2004 | Bost et al. | |
| 2005/0123445 | A1 | * | 6/2005 | Blecka | G01N 35/025 422/64 |
| 2006/0013729 | A1 | * | 1/2006 | Carey | B01F 9/0025 422/63 |
| 2014/0065017 | A1 | | 3/2014 | Herz et al. | |

FOREIGN PATENT DOCUMENTS

| | | | |
|---|---|---|---|
| CN | 104470455 | A | 3/2015 |
| EP | 0062251 | A1 | 10/1982 |
| GB | 2068115 | A | 8/1981 |
| JP | S56-150357 | A | 11/1981 |
| JP | S61-204566 | A | 9/1986 |
| JP | S64-044858 | A | 2/1989 |
| JP | H03-506075 | A | 12/1991 |
| JP | H08-194003 | A | 7/1996 |
| JP | 2013 156089 | A | 8/2013 |
| JP | 2013156089 | A * | 8/2013 |

OTHER PUBLICATIONS

Extended EP Search Report dated Feb. 13, 2019 of corresponding European Application No. 17753784.2, 4 Pages.

* cited by examiner

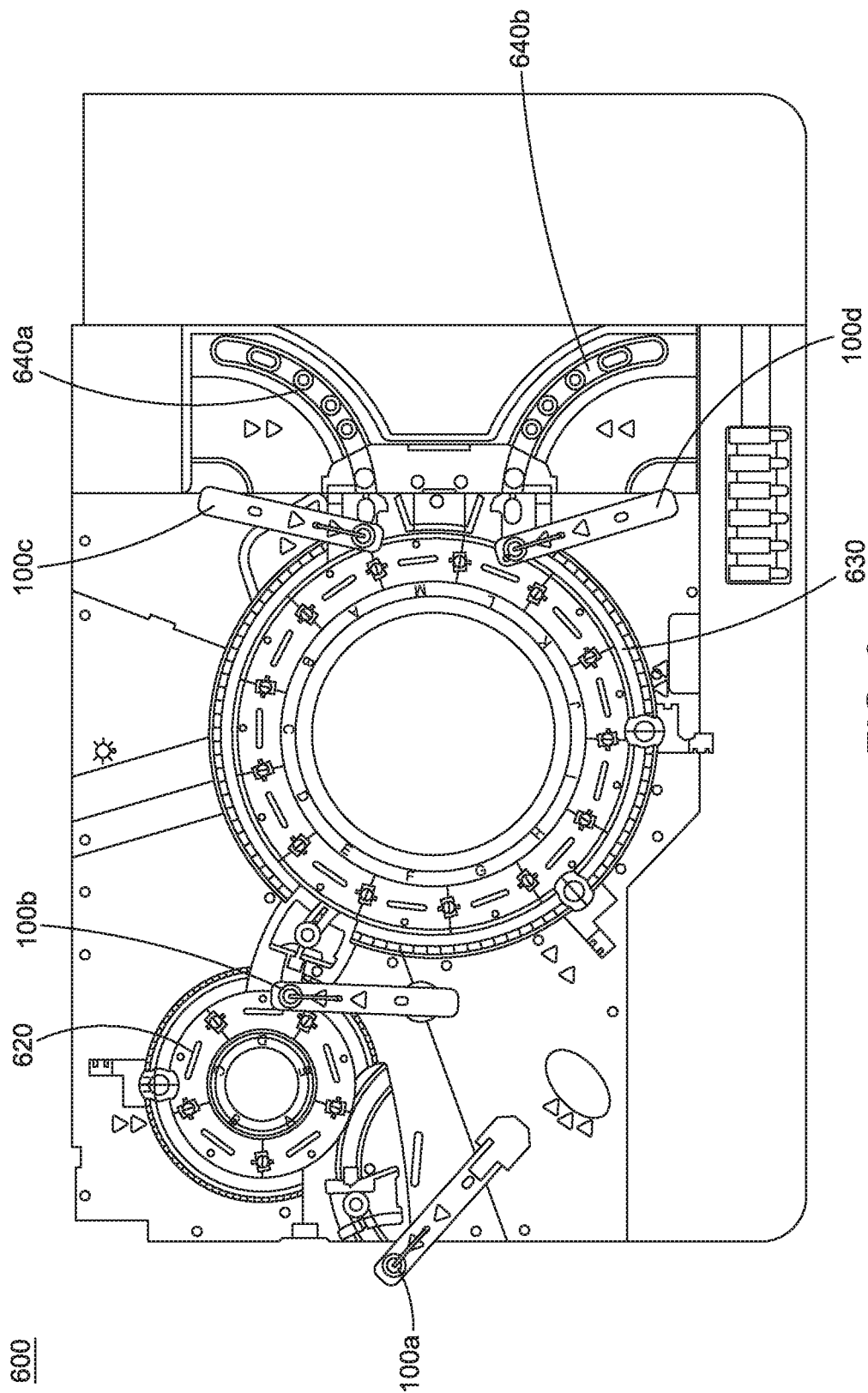

SINGLE-PIECE TRANSFER ARM STRUCTURE FOR ANALYTICAL INSTRUMENTATION

CROSS-REFERENCE TO RELATED APPLICATION

This application claims priority to U.S. provisional application Ser. No. 62/297,264 filed Feb. 19, 2016, the contents of which is incorporated herein by reference in its entirety.

TECHNOLOGY FIELD

The present invention relates generally to fluid transfer in an in vitro diagnostics environment.

BACKGROUND

Clinical analyzers typically utilize transfer arms to position a fluid transfer probe (or needle) and move the probe between fluid aspiration locations (e.g., a reagent container) and fluid dispense locations (e.g., a reaction vessel). Multiple transfer arms are typically used to handle various transfers during an analysis of a sample. Often, these transfer arms are radial in nature; they move the probe along a circular arc. For architectural reasons, however, the different transfer arms may require movement of the probe along arcs of varying radii. The radial component of the arm provides the structure needed to locate the probe at the correct radius with sufficient stiffness, and it should also be aesthetically pleasing. Achieving the above functions for minimal cost and with minimal number of components has been a challenge.

Previous transfer arm structures have included multiple parts—structural and aesthetic. Some examples include a metallic superstructure covered with a bolt-on thermoplastic aesthetic covering, or a two-piece clam-shell type structure. Additionally, to accommodate multiple arms requiring different radial lengths, unique components have been designed and manufactured. Such designs can be complex and costly.

Accordingly, an apparatus that overcomes these shortcomings is desired.

SUMMARY

Embodiments are directed to a single piece radial transfer arm in a clinical analyzer in an in vitro diagnostics (IVD) environment.

In an embodiment, the transfer arm comprises an elongated, rigid member comprising a top surface, a bottom surface, a pivot end, and a component end.

In an additional embodiment, the transfer arm comprises an elongated, rigid member comprising a top surface, a bottom surface comprising an underside portion of the top surface, sidewalls extending from the top surface and configured to form at least a partially surrounding enclosure for the bottom surface, a pivot end, and a component end.

In an embodiment, the pivot end comprises at least one radial configuration mounting location configured to secure a mounting clamp to the elongated, rigid member to couple a shaft to the elongated, rigid member. In an embodiment, the elongated, rigid member extends horizontally and the shaft is oriented substantially perpendicular to the elongated, rigid member.

In another embodiment, the pivot end comprises a plurality of radial configuration mounting locations to allow for respective ones of radial distances between a pivoting axis at the pivot end and an attached probe at the component end.

According to an embodiment, the component end comprises attachment locations for components to be secured to the transfer arm. The attachment locations may comprise one or more of (i) one or more access holes extending through the top surface and the bottom surface; and (ii) internal component mounting locations on the bottom surface. In an embodiment, the components comprise one or more of a probe, a crash detection mechanism, mixing devices, pick-and-place devices, circuit boards, and valves.

In yet another embodiment, the transfer arm further comprises electromagnetic interference (EMI) shielding material on at least a portion of the bottom surface.

In yet another embodiment, the transfer arm further comprises grounding material on at least a portion of the bottom surface.

The transfer arm, according to a further embodiment, comprises structural ribbing formed on the bottom surface, the structural ribbing configured to provide structural support for the elongated, rigid member.

In an embodiment, the elongated, rigid member is injection molded.

In an embodiment, the elongated, rigid member comprises a glass-filled nylon material.

In an additional embodiment, the transfer arm further comprises one or more alignment ribs formed on an outer portion of the sidewalls.

Additional features and advantages are apparent from the following detailed description that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 6 is a layout of an example system architecture within which embodiments of the invention may be implemented.

DETAILED DESCRIPTION

Embodiments are directed to a single piece radial transfer arm having an elongated, rigid member.

Figure 1A:
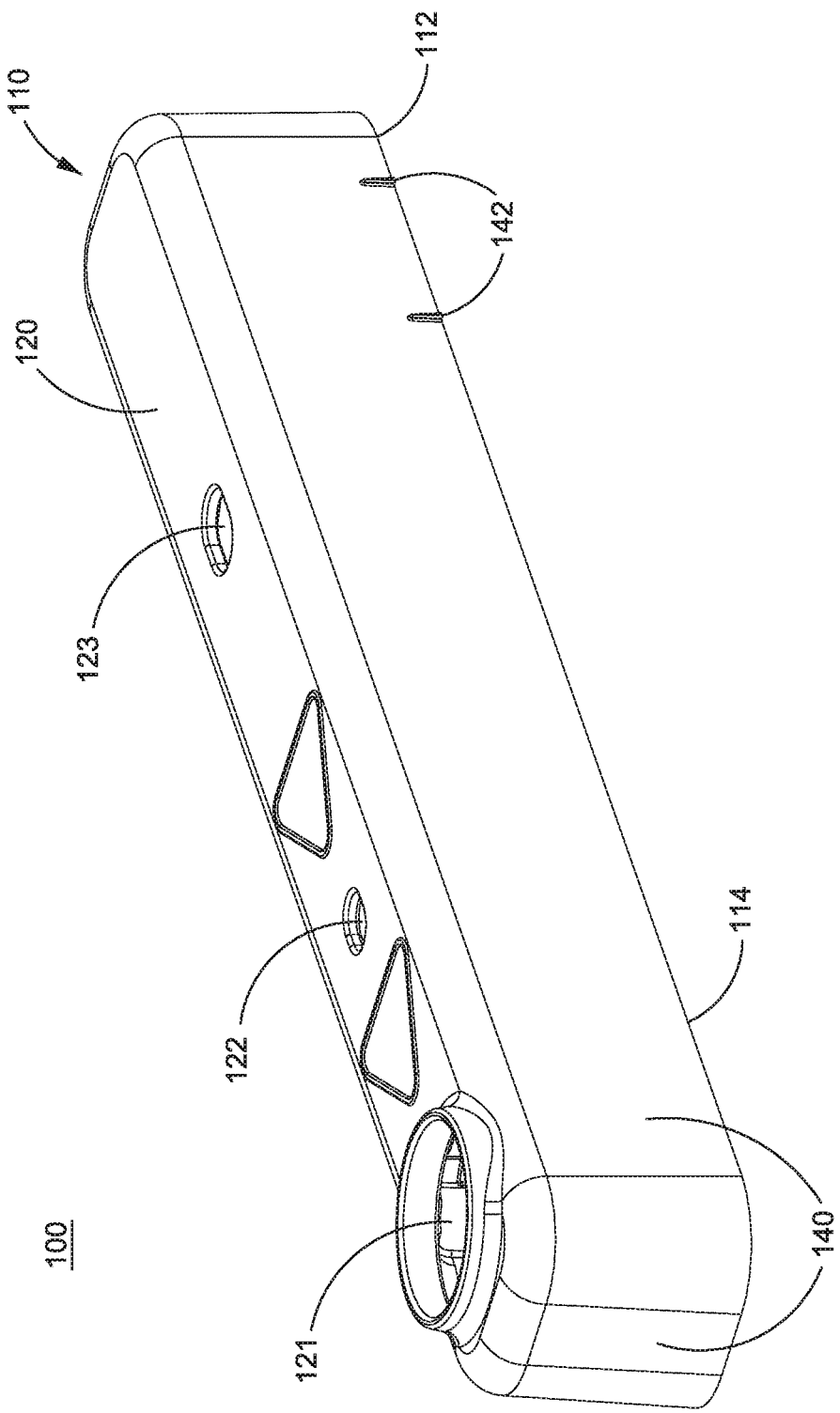
FIGS. 1A and 1B are diagrams illustrating top perspective views of a transfer arm, according to embodiments.
Figure 1B:
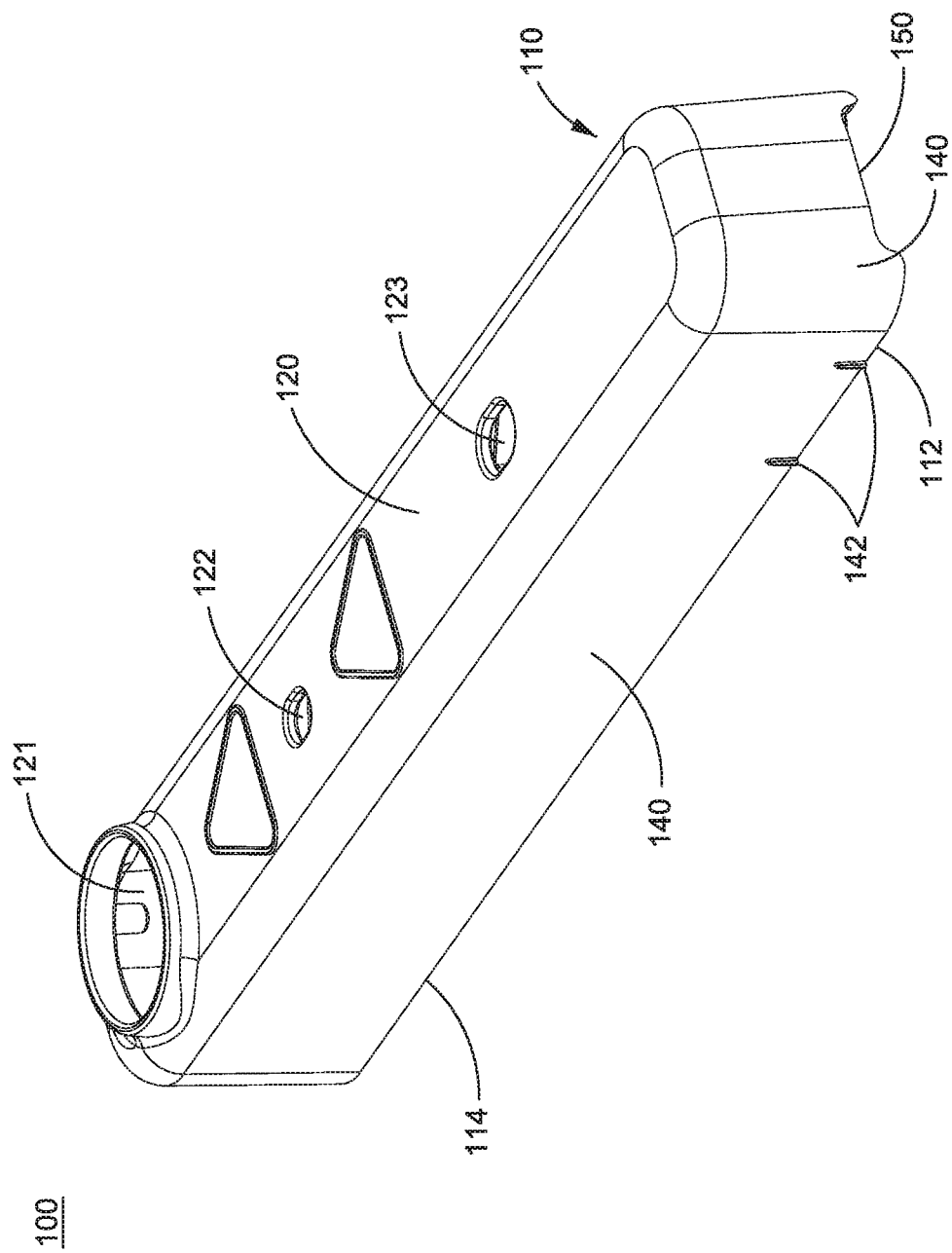
Figure 2:
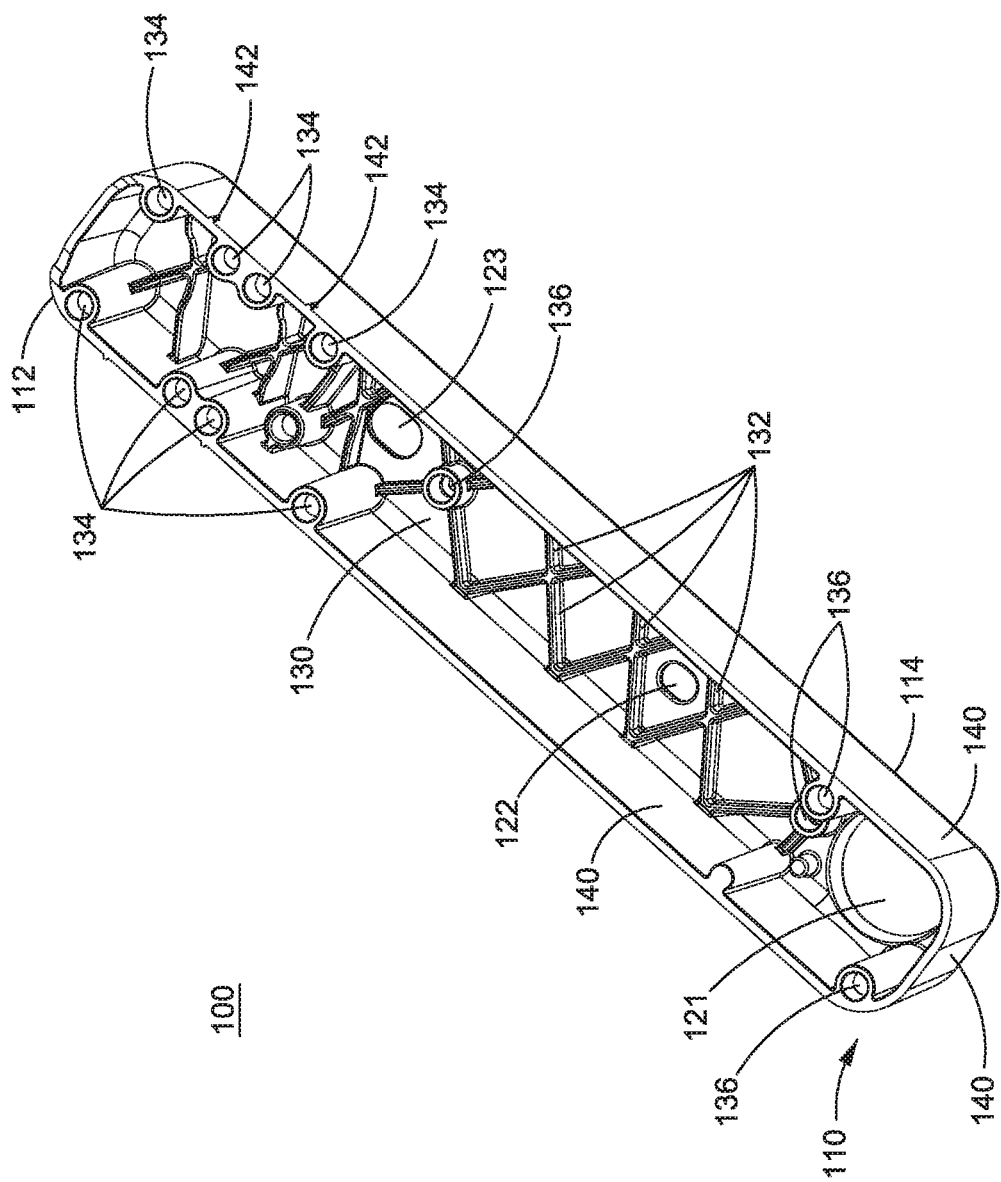
FIG. 2 is a diagram illustrating a bottom perspective view of a transfer arm, according to an embodiment.

FIGS. 1A and 1B are diagrams illustrating top perspective views of a transfer arm 100, according to embodiments. FIG. 2 is a diagram illustrating a bottom perspective view of the transfer arm 100 to show an underside view of the transfer arm 100, according to an embodiment. The transfer arm 100 is comprised of a chassis or elongated, rigid member 110 that provides structural and aesthetic properties, acting as both a mounting base and a cover for transfer arm components. The elongated, rigid member 110 is a single component, such as a single piece of injection-molded plastic. As shown in FIGS. 1A, 1B, and 2, the elongated, rigid member 110 has a top surface 120, a bottom or underside surface 130, and sidewalls 140. The bottom or underside surface 130 is an underside portion of the top surface 120, and the sidewalls 140 extend from the top surface 120 and form at least a partially surrounding enclosure for the bottom surface 130. The elongated, rigid member 110 has a pivot end 112 and a component end 114.

As shown in FIGS. 1A and 1B, one or more access holes (such as probe access hole 121, sized and positioned for a probe and its mounting assembly, and tubing access hole 122, sized and positioned for tubing that interfaces to the probe (see, for example, FIGS. 4A and 4B)) extend through the top surface 120 and the bottom surface 130 of the elongated, rigid member 110 of the transfer arm 100. Access hole 123 is also provided. In an embodiment, probe access hole 121 and tubing access hole 122 are provided at the component end 114 portion of the elongated, rigid member 110; and access hole 123 is provided near the pivot end 112. Other access holes and configurations thereof may be provided depending on use and design factors for which the transfer arm 100 is being utilized.

As shown in FIG. 1B, an injection gate location 150 is provided. The injection gate location 150 provides for symmetric mold flow and limits part warping, while being unobtrusive for the aesthetics of the transfer arm 100. Other gate locations that achieve a symmetrical part are possible and may be implemented for the transfer arm 100.

As shown in the underside view of the transfer arm 100 of FIG. 2, structural ribbing 132 is formed on the bottom surface 130. The size, shape, and location of the structural ribbing 132 is such that it provides structural support for the elongated, rigid member 110. Variations of the structural ribbing 132 shown in FIG. 2 may be used.

Figure 3:
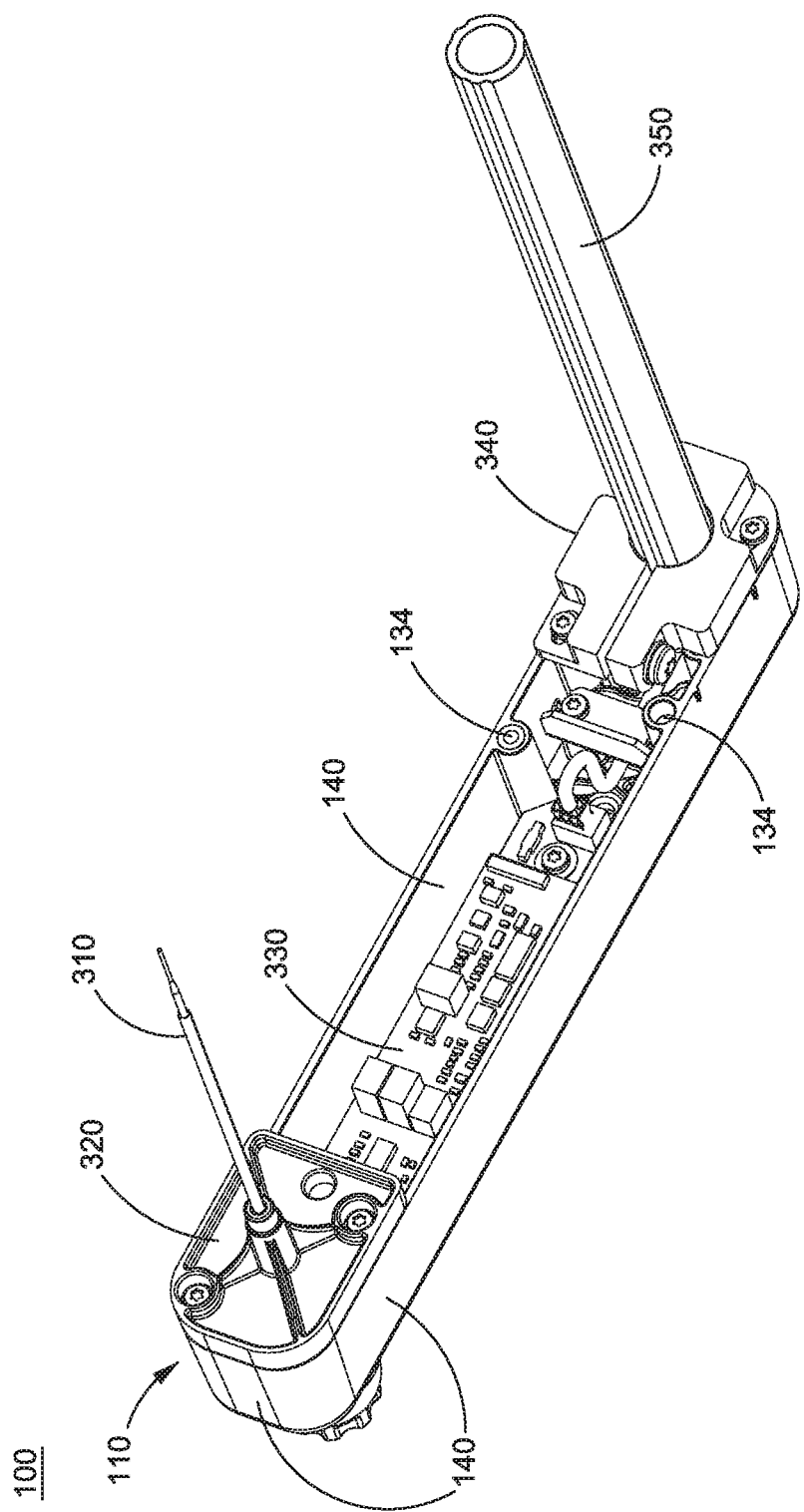
FIG. 3 is a diagram illustrating a bottom perspective view of a transfer arm with mounted components, according to an embodiment.

As shown in FIG. 2, internal component mounting locations 136 are provided on the bottom surface 130 of the elongated, rigid member 110. FIG. 3 provides a bottom perspective view of the transfer arm 100 with mounted components mounted via the internal component mounting locations 136. In this exemplary configuration are a probe 310 with tubing 312 mounted via a probe mounting assembly 320 and a printed circuit assembly 330. Various screws or the like are used to connect the components (e.g., the probe mounting assembly 320 and the printed circuit assembly 330) to the bottom surface 130 via the internal component mounting locations 136.

Figure 4A:
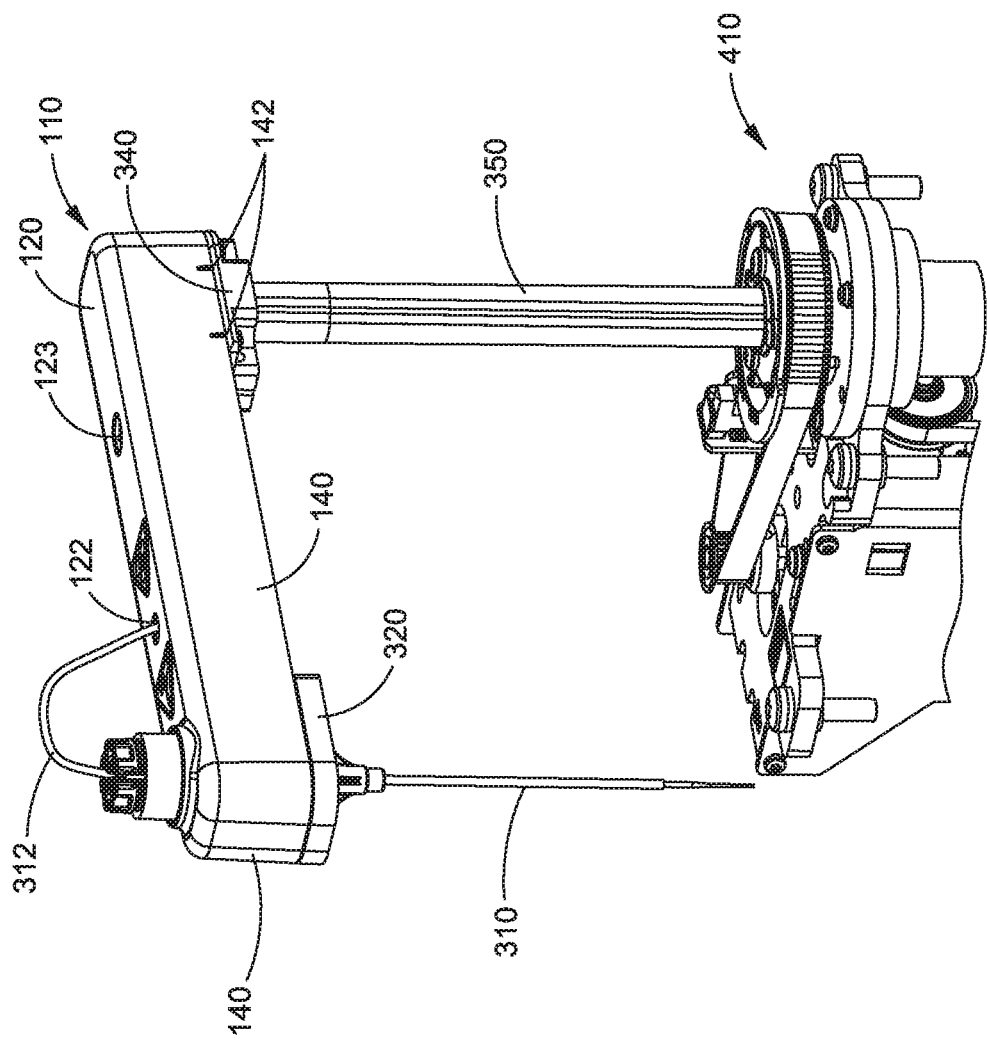
FIGS. 4A and 4B are diagrams illustrating a transfer arm mounted in a long and short radial dimension configuration, respectively, according to embodiments.
Figure 4B:
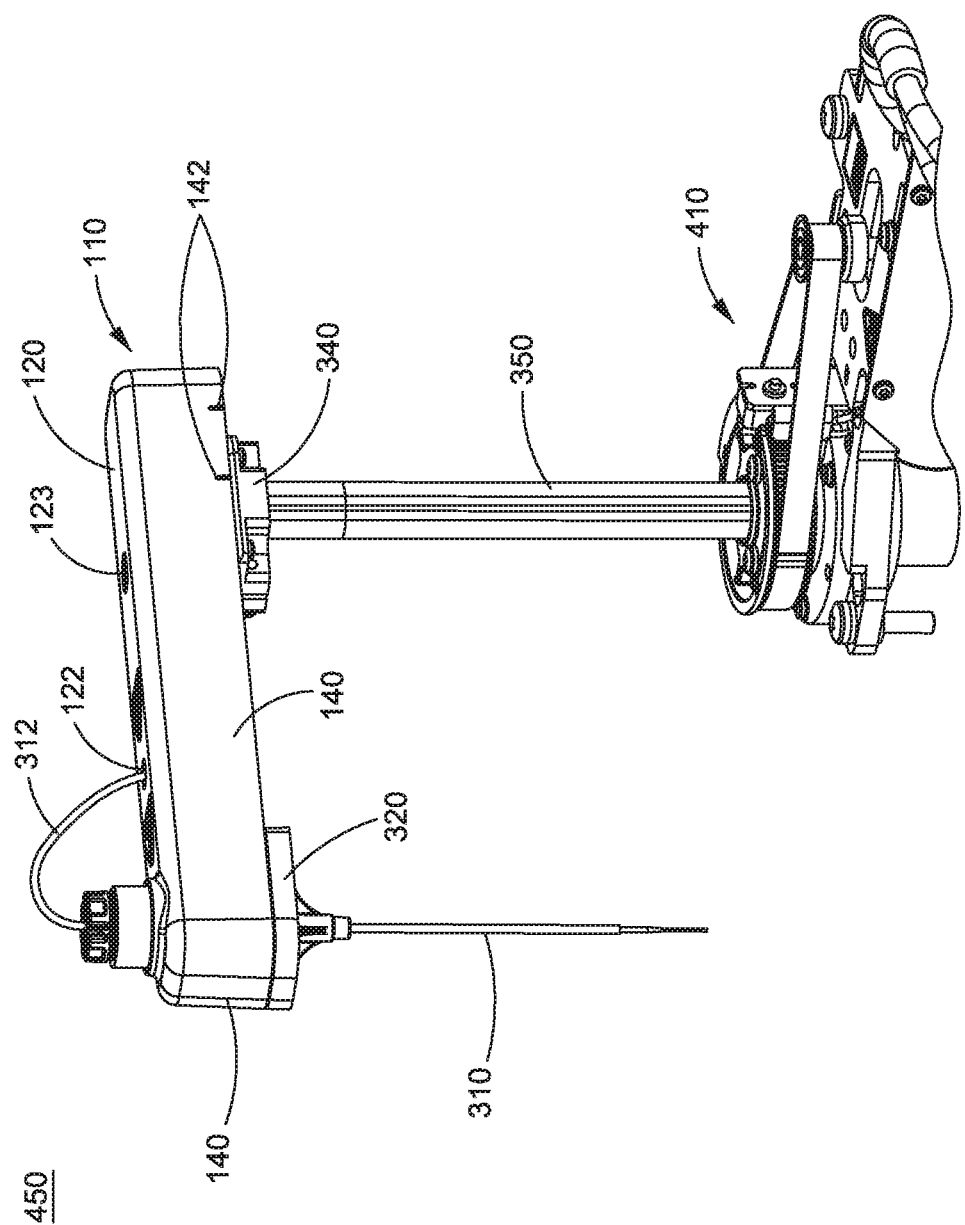

Turning back to FIG. 2, shown are a plurality of radial configuration mounting locations 134 provided on the bottom surface 130 to allow for multiple radial distances between a pivoting axis of the transfer arm 100 (at the pivot end 112) and an attached probe (e.g., probe 310) to accommodate arcs of different radii. This concept is illustrated in FIGS. 4A and 4B, which illustrate the transfer arm 100 mounted in a long radial dimension configuration 400 (see FIG. 4A) and in a short radial dimension configuration 450 (see FIG. 4B). Thus, the same component (i.e., the transfer arm 100) can be reused as all transfer arms on an analyzer.

With reference to FIGS. 3, 4A, and 4B, a mounting clamp 340 that couples a shaft 350 to the elongated, rigid member 110 is mounted via the radial configuration mounting locations 134.

FIGS. 4A and 4B also illustrate a drive mechanism or motor controller 410 coupled to the shaft 350 to drive rotational and vertical movement of the transfer arm 100.

Alignment ribs 142 formed on a portion of sidewalls 140 are provided, according to an embodiment, as markings for use as alignment aids for both gross and fine adjustment (see FIGS. 1A-5). In other embodiments, indentations, notches, embossed lettering, and the like may alternatively or additionally be used to indicate alignment position(s).

Figure 5:
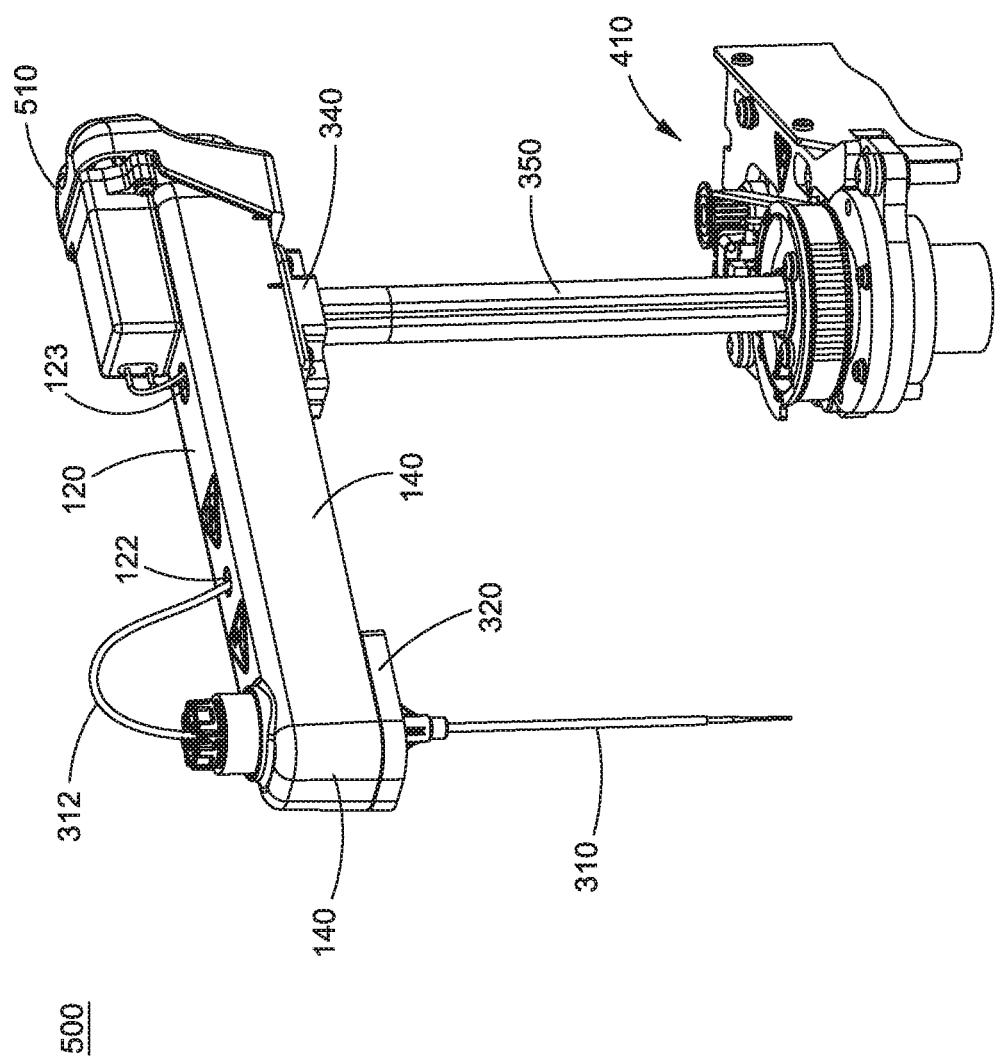
FIG. 5 is a diagram illustrating a transfer arm with an externally mounted manifold and valve, according to an embodiment.

FIG. 5 is a diagram 500 illustrating a transfer arm 100 with an externally mounted manifold and valve 510, according to an embodiment. The access hole 123 is provided for wires of the manifold and valve 510, which may be mounted using the mounting locations 134 and/or 136. FIG. 5 also illustrates the drive mechanism or motor controller 410 coupled to the shaft 350.

Other devices can also be mounted, according to embodiments, using the mounting locations 134 and/or 136, including, for example and not limitation, a crash detect mechanism, a mixing device, a pick-and-place device, a capacitive level detection printed circuit assembly, other circuit boards, and liquid valves. Many of these components are contained within the aesthetic enclosure provided by the sidewalls 140. In other words, the components are hidden or at least partially hidden from view, depending on geometries and orientations of the components and/or the transfer arm 100.

In an embodiment, adjustable mounting can take many forms; for example, slots in the transfer arm 100 or a threaded fine adjustment knob. Additional specific or universal mounting points or access holes may be added.

In an embodiment, the material of the transfer arm 100 may be a glass-filled nylon to provide the necessary stiffness and strength. The material can be color-matched and textured, as desired, eliminating the need for paint. The design of the mold for manufacturing the transfer arm 100 is an important factor in producing a flat part that positions a probe perpendicular to the plane of travel (see FIG. 1B). Other aesthetic properties may include texturing of the upper, outside surfaces (i.e., the top surface 120 and/or the sidewalls 140) of the single-piece transfer arm 100, aesthetically pleasing lines, and surfaces for information labels (e.g., hazard and warning labels).

In an embodiment, an interior portion of the transfer arm 100 (e.g., a portion of the bottom surface 130 and/or an interior portion of the sidewalls 140) may be coated with an electrically conductive paint to provide for electromagnetic interference (EMI) protection (by creating a partial faraday cage) for critical electrical components mounted within. Such a coating may also provide a chassis ground path to the shaft 350 of the arm for a circuit board and other components. In another embodiment, an interior portion of the transfer arm 100 (e.g., a portion of the bottom surface 130 and/or an interior portion of the sidewalls 140) may be coated with a grounding material.

According to embodiments provided herein, the transfer arm 100 has an advantage of low cost. This includes the part cost, assembly cost (fewer components), and lower inventory costs for manufacturing and service (again due to fewer components). A technical feature that contributes to this lower cost advantage is that the transfer arm 100, according to embodiments herein, is a single part. It is injection molded, which is a low-cost process, and it can be re-used in multiple applications. Savings compared to traditional methods can range from hundreds of thousands to over a million dollars per year, depending on production quantities and on how many products transfer arm 100 is applied.

FIG. 6 provides a layout of an example system architecture 600 within which embodiments of the invention may be implemented. Shown in FIG. 6 are various transfer arms 100 (100a, 100b, 100c, and 100d) with respective probes; a diluting turntable 620 including a plurality of diluting containers arranged in one or more diluting rings; a reaction turntable 630 including a plurality of reaction containers arranged in one or more reaction rings; and reagent storage areas 640a and 640b dedicated to storage and supply of a respective reagent, each reagent storage area 640a and 640b including a plurality of reagent containers. In operation, transfer arm 100a and its respective probe may operate to transfer sample from an access position to one or more diluting containers on the diluting turntable 620 to create a dilution therein. Transfer arm 100b and its respective probe may operate to transfer dilution from a diluting container to a reaction container on the reaction turntable 630. Transfer arms 100c and 100d and their respective probes may operate to transfer a reagent from reagent storage area 640a and 640b, respectively, to a reaction container on the reaction turntable 630. The various transfers occur by use of a pumping mechanism, such as a displacement pump, for example, attached to the transfer arms 100. Additionally, the system architecture 600 includes one or more controllers for controlling operation of the various components, including the transfer arms 100 (e.g., drive mechanism or motor controller 410), the probes, and the turntables.

The system architecture 600 of FIG. 6 and the accompanying description are purely exemplary and non-limiting to the single piece radial transfer arm disclosed herein. The system architecture 600 is just one example system in which the single piece radial transfer arm may be utilized.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A single piece radial transfer arm for a clinical analyzer in an in vitro diagnostics (IVD) environment, the transfer arm comprising:
an elongated, rigid member comprising:
a top surface;
a bottom surface;
a pivot end comprising a plurality of radial configuration mounting locations provided on the bottom surface of the elongated, rigid member, wherein each of the plurality of radial configuration mounting locations are configured to secure the elongated, rigid member to an end of a shaft such that the elongated, rigid member can revolve about a center axis of the end of the shaft, wherein the plurality of radial configuration mounting locations allow for respective ones of radial distances between a pivoting axis at the pivot end and at least one attachment location at a component end; and
the component end comprising the at least one attachment location configured to secure at least one component to the elongated, rigid member.

2. The transfer arm of claim 1, wherein at least one of the plurality of radial configuration mounting locations are configured to secure a mounting clamp to the elongated, rigid member to couple the end of the shaft to the elongated, rigid member.

3. The transfer arm of claim 1, wherein the at least one attachment location is configured to secure to the elongated, rigid member one or more of a probe, a crash detection mechanism, mixing devices, pick-and-place devices, circuit boards, and valves.

4. The transfer arm of claim 1, further comprising one or more of electromagnetic interference (EMI) shielding material on at least a portion of the bottom surface and grounding material on at least a portion of the bottom surface.

5. The transfer arm of claim 1, wherein the elongated, rigid member is injection molded.

6. A single piece radial transfer arm in a clinical analyzer in an in vitro diagnostics (IVD) environment, the transfer arm comprising:
an elongated, rigid member comprising:
a top surface;
a bottom surface comprising an underside portion of the top surface;
sidewalls extending from the top surface and configured to form at least a partially surrounding enclosure for the bottom surface;
a pivot end comprising a plurality of radial configuration mounting locations provided on the bottom surface of the elongated, rigid member, wherein each of the plurality of radial configuration mounting locations are configured to secure the elongated, rigid member to an end of a shaft such that the elongated, rigid member can revolve about a center axis of the end of the shaft, wherein the plurality of radial configuration mounting locations allow for respective ones of radial distances between a pivoting axis at the pivot end and at least one attachment location at a component end; and
the component end comprising the at least one attachment location configured to secure at least one component to the elongated, rigid member.

7. The transfer arm of claim 6, wherein at least one of the plurality of radial configuration mounting locations are configured to secure a mounting clamp to the elongated, rigid member to couple the end of the shaft to the elongated, rigid member.

8. The transfer arm of claim 7, wherein the elongated, rigid member extends horizontally and the shaft is oriented substantially perpendicular to the elongated, rigid member.

9. The transfer arm of claim 6, wherein the at least one attachment location comprise; one or more of: (i) one or more access holes extending through the top surface and the bottom surface; and (ii) internal component mounting locations on the bottom surface.

10. The transfer arm of claim 6, wherein the at least one attachment location is configured to secure to the elongated, rigid member one or more of a probe, a crash detection mechanism, mixing devices, pick-and-place devices, circuit boards, and valves.

11. The transfer arm of claim 6, further comprising electromagnetic interference (EMI) shielding material on at least a portion of the bottom surface.

12. The transfer arm of claim 6, further comprising grounding material on at least a portion of the bottom surface.

13. The transfer arm of claim 6, further comprising structural ribbing formed on the bottom surface, the structural ribbing configured to provide structural support for the elongated, rigid member.

14. The transfer arm of claim 6, wherein the elongated, rigid member is injection molded.

15. The transfer arm of claim 6, wherein the elongated, rigid member comprises a glass-filled nylon material.

16. The transfer arm of claim 6, further comprising one or more alignment ribs formed on an outer portion of the sidewalls.

* * * * *